United States Patent [19]

Turi

[11] 4,083,974

[45] Apr. 11, 1978

[54] TOPICAL STEROIDAL ANTI-INFLAMMATORY PREPARATIONS CONTAINING POLYOXYPROPYLENE 15 STEARYL ETHER

[75] Inventor: Joseph S. Turi, Portage, Mich.

[73] Assignee: The Upjohn Company, Kalamazoo, Mich.

[21] Appl. No.: 774,753

[22] Filed: Mar. 7, 1977

[51] Int. Cl.$^2$ ............................................. A61K 31/58
[52] U.S. Cl. .................................... 424/241; 424/243; 424/81
[58] Field of Search ................................ 424/241, 243

[56] References Cited

U.S. PATENT DOCUMENTS

| 3,981,996 | 9/1976 | Leigh ................................... 424/242 |
| 4,017,615 | 4/1977 | Shastri et al. ......................... 424/242 |

*Primary Examiner*—Elbert L. Roberts
*Attorney, Agent, or Firm*—Bruce Stein; Roman Saliwanchik

[57] ABSTRACT

The present invention discloses topical preparations containing anti-inflammatory steroids. These may be ointments or solutions which contain as a solubilizing agent for the steroid, polyoxypropylene 15 stearyl ether.

13 Claims, No Drawings

TOPICAL STEROIDAL ANTI-INFLAMMATORY PREPARATIONS CONTAINING POLYOXYPROPYLENE 15 STEARYL ETHER

BACKGROUND OF THE INVENTION

Many pharmaceutical compositions containing steroidal anti-flammatory agents are available for topical application. These include ointments, creams, lotions, solutions, etc. See Physician's Desk Reference (PDR) 1976, 30th Edition, Medical Economics Company, New Jersey. In particular, many pharmaceutical ointments containing topical anti-flammatory steroids for topical application are known. For example, triamcinolone acetonide, fluocinonide, fluocinolone acetonide, hydrocrotisone acetate, methylprednisolone acetate, and hydrocortisone. See PDR, supra, pages 872, 1528, 1529, 1569, 1581, and 1194, respectively.

In general, the commercial anti-inflammatory pharmaceutical compositions all contain an anti-inflammatory steroid, which are useful when applied topically, and a pharmaceutical acceptable carrier for applying the anti-inflammatory steroid topically.

U.S. Pat. No. 3,180,797 discloses a pharmaceutical composition containing an anti-inflammatory steroid in an aqueous solution. The pharmaceutical compositions of the present invention contain no water.

U.S. Pat. No. 3,352,753 discloses pharmaceutical compositions for topical application comprising a corticosteroid in a gel form. The present invention does not include gels.

U.S. Pat. No. 3,867,528 discloses a topical cream composition useful for administering anti-inflammatory steroids topically. The cream formulation contains ethoxylated stearyl alcohol, benzyl alcohol, isopropylpalmitate, glycerine, and sorbitol solution. The present invention contains none of these ingredients.

U.S. Pat. Nos. 3,749,773, 3,892,586, 3,892,587, and 3,934,013 all disclose pharmaceutical compositions for administering an anti-inflammatory steroid topically. All four patents disclose the use of the propylene glycol as a solvent for the steroids. U.S. Pat. No. 3,749,773 discloses that the composition has the property of possessing anti-bacterial activity. This is not surprising or unexpected in view of the fact that the composition contains approximately 15% of ethyl alcohol which is known anti-bacterial agent. U.S. Pat. No. 3,892,857 differs from the present invention in that it discloses besides the anti-inflammatory steroid the other major ingredients are propylene glycol and water. The present invention contains no water. The propylene glycol utilized in the four above-identified U.S. patents was used as a solvent to dissolve the steroid. Propylene glycol is known to be a good solvent. However, it also possesses two very undesirable qualities from a pharmacological point of view. These are (1) that it is irritating to the skin and (2) that it is a non-lubricant. Therefore, there is a need to find a solvent which is suitable for dissolving an anti-inflammatory steroid which is non-irritating and which has lubricant properties.

The present invention discloses such a solvent, polyoxypropylene 15 stearyl ether.

Polyoxypropylene 15 stearyl ether is marketed under the trademark Arlamol ® E by Imperial Chemical Industries (ICI) as an emollient solvent for cosmetic products. It is disclosed as being an emollient, a lubricant, and a solvent useful in cosmetic products such as bath oils, sunscreens, hair products, aerosol, anti-perspirants, and hand and body lotions.

There is no disclosure in any manner whatsoever of using polyoxypropylene 15 stearyl ether as a solvent in pharmaceutical preparations with anti-inflammatory steroids for topical administration.

SUMMARY OF THE INVENTION

The present invention is a pharmaceutical composition for topical application comprising an anti-inflammatory steroid, polyoxypropylene 15 stearyl ether and a pharmaceutically acceptable carrier(s). This pharmaceutical composition has the advantage of being non-irritating and having lubricant properties. In addition, it surprisingly and unexpectedly has been found to be anti-bacterial and anti-fungal. When polyoxypropylene 15 stearyl ether is present in a concentration greater than or equal to 15% no preservative is needed. When it is present in less than 15% concentration, less preservative is needed than would be if no polyoxypropylene 15 stearyl ether was present. This not only saves on cost of manufacture but also exposes the inflamed tissue to be treated to fewer external chemical compounds. The anti-bacterial, anti-fungal properties while not sufficiently great to be of therapeutic value are sufficient to allow the compounding, manufacture, and sale of the present composition without addition of any preservatives when the polyoxypropylene 15 stearyl ether is present in concentration greater than or equal to 15%.

Disclosed is a pharmaceutical composition for topical application selected from the group consisting of ointments and non-aqueous solutions which comprises an anti-inflammatory effective amount of an anti-inflammatory steroid, polyoxypropylene 15 stearyl ether and pharmaceutically acceptable carriers.

The definitions and explanations below are for the terms as used throughout the entire patent application including both the specification and the claims.

All temperatures are in degrees Centigrade.

Polyoxypropylene 15 stearyl ether includes Arlamol ® E (ICI).

U.S.P. refers to the United States Pharmacopeia.

N.F. refers to the National Formulary.

Pharmaceutically acceptable refers to those properties and/or substances which are acceptable to the patient from a pharmacological-toxicological point of view and to the manufacturing pharmaceutical chemist from a physical-chemical point of view regarding composition formulation, stability, patient acceptability and bioavailability.

Diflorasone diacetate refers to $6\alpha,9\alpha$-difluoro-$11\beta,17\alpha,21$-trihydroxy-$16\beta$-methylpregna-1,4-diene-3,20-dione 17,21-diacetate, U.S. Pat. No. 3,980,778.

Betamethasone valerate refers to $9\alpha$-fluoro-$11\beta,17\alpha,21$-trihydroxy-$16\beta$-methylpregna-1,4-diene-3,20-dione 17-valerate.

Fluocinonide refers to $6\alpha,9\alpha$-difluoro-$11\beta,16\alpha,17\alpha,21$-tetrahydroxypregna-1,4-diene-3,20-dione cyclic 16,17-acetal with acetone 21-acetate.

Clobetasol propionate refers to 21-chloro-$9\alpha$-fluoro-$11\beta,17\alpha$-dihydroxy-$16\beta$-methylpregna-1,4-diene-3,20-dione 17-propionate.

Methylprednisolone acetate refers to $11\beta,17\alpha,21$-trihydroxy-$6\alpha$-methylpregna-1,4-diene-3,20-dione 21-acetate.

Fluorometholone refers to $9\alpha$-fluoro-$11\beta,17\alpha$-dihydroxy-$6\alpha$-methylpregna-1,4-diene-3,20-dione.

Fluocinolone acetonide refers to 6α,9α-difluoro-11β,16α,17α,21-tetrahydroxypregna-1,4-diene-3,20-dione cyclic 16,17-acetal with acetone.

Hydrocortisone acetate refers to 11β,17α,21-trihydroxypregna-4-ene-3,20-dione 21-acetate.

Fludrocortisone refers to 9α-fluoro-11β,17α,21-trihydroxypregna-4-ene-3,20-dione.

Flumethasone refers to 6α,9α-difluoro-11β,17α,21-trihydroxy-16α-methylpregna-1,4-diene-3,20-dione.

Triamcinolone acetonide refers to 9α-fluoro-11β,16α,17α,21-tetrahydroxypregna-1,4-diene-3,20-dione cyclic 16,17-acetal with acetone Hydrocortisone refers to 11β,17α,21-trihydroxypregna-4-ene-3,20-dione.

DETAILED DESCRIPTION OF THE INVENTION

The pharmaceutical composition of the present invention is selected from the group consisting of ointments and non-aqueous solutions. It is preferred that the phamaceutical composition be an ointment.

The scope of the present invention includes various anti-inflammatory steroids which have been used in topical preparations for treating inflammatory conditions. Examples of these anti-inflammatory steroids for topical administration include (reference is page number of 1976 PDR, supra) hydrocortisone acetate (p. 1587 and 1569), betamethasone valerate (p. 1398), fluocinonide (p. 1528), fluocinolone acetonide (p. 1529), betamethasone (p. 1354), methylprednisolone acetate (p. 1581), fluorometholone (p. 1596), hydrocortisone (p. 1194), and triamcinolone acetonide (pp. 869 and 1477). Preferably the anti-inflammatory steroid is selected from the group consisting of diflorasone diacetate, betamethasone valerate, fluocinonide, clobetasol propionate, methylprednisolone acetate, fluorometholone, fluocinolone acetonide, hydrocortisone acetate, fludrocortisone, flumethasone, and triamcinolone acetonide. More preferably the anti-inflammatory steroid is selected from the group consisting of diflorasone diacetate, betamethasone valerate, fluocinonide, fluocinolone acetonide, or clobetasol propionate. It is most preferred that the anti-inflammatory steroid is diflorasone diacetate.

The anti-inflammatory effective amount of the anti-inflammatory steroids of the present invention will vary depending upon the particular steroid, the nature of the disease and the condition of the patient or animal to be treated. The concentration of the anti-inflammatory steroid is between 0.005 and 0.10%. Preferably, the concentration of the effective amount of the anti-inflammatory steroid is between 0.01 and 0.05%. For diflorasone diacetate the preferred concentration is 0.01–0.10%.

The concentration of the anti-inflammatory steroid throughout the topical pharmaceutical preparation must be uniform.

The actual concentration of the anti-inflammatory steroid is adjusted so that an effective amount to produce the desired anti-inflammatory effect will be delivered when a specified amount of the topical pharamaceutical preparation is applied locally. The exact dose depends on the condition of the patient or animal.

Polyoxypropylene 15 stearyl ether is a mixture of various length propylene oxide units with long chain fatty alcohols. More particularly, the number of propylene oxide units per long chain fatty alcohol is from 4 to 20 with the average being 15. Stearyl alcohol is the long chain fatty alcohol. Therefore, polyoxypropylene 15 stearyl ether is approximately 95% 15 propylene oxide units per stearyl alcohol unit, connected to the stearyl alcohol by an ether linkage. The product is well known to those skilled in the art of formulating and compounding topical ointment like compositions and preparations and there is no ambiguity as to what is meant by polyoxypropylene 15 stearyl ether to one skilled in the art.

Polyoxypropylene 15 stearyl ether has the following properties as described in the literature sheet 102-1 (LD-142 Revised) supplied by ICI United States for polyoxypropylene 15 stearyl ether (Arlamol ® E).

| GENERAL CHARACTERISTICS | |
| --- | --- |
| Classification | Emollient-solvent |
| Form at 25° C. | Oily liquid |
| Color | Colorless to light yellow |
| Odor | Slight characteristic |
| Iodine Value | Typically below 3.0 |
| Viscosity at 25° C. | Approx. 90 cps. |
| Pour Point | Typically below 0° C. |
| Specific Gravity at 25° C./25° C. | Approx. 0.95 |
| Flash Point | Approx. 232° C. |
| Cloud Point (as is) | Approx. 2° C. |
| Spreading Coefficient (25° C.) | Approx. +33.8 dynes/cm. |
| Alkali Sensitivity | Stable |
| SOLUBILITIES | |
| (a) Soluble in mineral oil, isopropyl esters, cottonseed oil, ethanol, isopropanol, hexadecyl alcohol. | |
| (b) Insoluble in water, propylene glycol and glycerin. | |
| SPECIFICATIONS | |
| Water Content, % | 0.7 max. |
| Hydroxyl Number | 62–77 |
| Acid Number | 2.0 max. |

The amount of polyoxypropylene 15 stearyl ether used in the pharmaceutical compositions of the present invention is an amount sufficient to dissolve the anti-inflammatory steroid and keep it in solution. The amount of polyoxypropylene 15 stearyl ether used in the pharmaceutical composition of the present invention will therefore depend upon the solubility of the particular anti-inflammatory steroid in the polyoxypropylene 15 stearyl ether and the amount of that anti-inflammatory steroid in the pharmaceutical composition. The amount of polyoxypropylene 15 stearyl ether in the ointment pharmaceutical compositions of the present invention is between 1 to 40% (w/w), more preferred 5 to 20% (w/w).

Polyoxypropylene 15 stearyl ether surprisingly and unexpectedly has been found to be anti-bacterial and anti-fungal. While the anti-bacterial and anti-fungal properties of polyoxypropylene 15 stearyl ether are not sufficiently great to be of therapeutic value they are sufficient to permit the compounding, manufacture and sale of the ointment compositions of the present invention without the addition of any preservatives when polyoxypropylene 15 stearyl ether is present in an amount greater than or equal to 15%. When it is present in a concentration of at least 15% no preservatives need be added to the pharmaceutical compositions of the present invention. When it is present in a concentration less than 15%, preservatives should be added but in amounts less than if no polyoxypropylene 15 stearyl ether was present.

The pharmaceutical compositions of the present invention can be ointments or solutions. The appropriate pharmaceutical acceptable carriers for each type of pharmaceutical composition are by definition different. Pharmaceutically acceptable as used in this patent application refers to those properties and/or substances which are acceptable to the patient from a pharmacological-toxicological point of view and to the manufacturing pharmaceutical chemist from a physical-chemical point of view regarding composition formulation, stability, patient acceptability and bioavailability.

Ointments are oleoginous preparations in which pharmaceutically acceptable carriers include non-emulsion ointment bases. Non-emulsion ointment bases include for example white ointment, yellow ointment, petrolatum, white petrolatum, and hydrous lanolin. The ointment base is present in 20–98% (w/w), preferably 30–80% (w/w).

In addition to the non-emulsion ointment bases the ointments also may include a number of other non-therapeutic ingredients which are used to effect the consistency of the product and the stability of the product. In the present invention these ingredients include stearic acid, stearyl alcohol, cetyl palmitate, isopropyl palmitate, cetyl alcohol, and glyceryl monostearate.

| Ingredients | % w/w |
| --- | --- |
| Stearic acid | 5–20 |
| Stearyl alcohol | 5–20 |
| Cetyl palmitate | 5–20 |
| Isopropyl palmitate | 5–20 |
| Cetyl alcohol | 5–20 |
| Glyceryl monostearate | 5–20 |

In addition to the above-mentioned non-therapeutic ingredients which are well-known components of ointment formulations, a number of multi-sterol extracts and lanolin derivatives may be added to the ointment formulations of the present invention. It is not necessary that the multi-sterol extracts and lanolin derivatives be added to the ointment formulations. See Examples 1 and 4–6. When present they are added because of their emulsifying and emollient properties which in some cases make for a more esthetically elegant pharmaceutical ointment. They do not affect the therapeutic efficacy of the composition.

The multi-sterol extracts and lanolin derivatives are marketed by a number of companies. For example, Amerchol, Amerchol Park, Edison, N.J., U.S.A.; Malmstrom Chemical Corp., 1501 W. Elizabeth Avenue, Linden, N.J. 07036, U.S.A.; Fanning Chemical Co., 357 W. Erie Street, Chicago, Ill. 60610, U.S.A.; Walter H. Jelly Co., Inc., 2822 Birch Street, Franklin Park, Ill., 60131, U.S.A. and R.I.T.A. Chemical Corp., 612 N. Michigan Avenue, Chicago, Ill. 60611, U.S.A. While there are differences between the lanolin products (multi-sterol extracts) of the various companies these differences are not critical. The differences are not major and the products of one company may be readily substituted for the product of another company in the ointment formulations of the present invention. The use of these multi-sterol extracts is well known to those skilled in the art of developing and formulating ointment pharmaceutical compositions. Examples of the multi-sterol extracts are set forth below.

A multi-sterol extract containing highly surface active selected lanolin sterols and complex higher alcohols in their free forms only is sold under the trademark Amerchol ® L-101 by Amerchol, Amerchol Park, Edison, N.J., U.S.A. It is an anhydrous, oil-miscible, water-dispersible, low-viscosity fluid. The product is widely used in emulsions and topical pharmaceuticals.

Amerchol ® L-101 has the following properties as described in the Amerchol Laboratory Handbook for Cosmetics and Pharmaceuticals supplied by Amerchol in 1977:

| | |
| --- | --- |
| Appearance | pale yellow, oily liquid |
| Odor | faint, chracteristic sterol odor |
| Water soluble acids and alkalies (USP XVI, p. 805) | neutral to litmus |
| Acid no. | 1.0 max. |
| Ash | 0.2% max. |
| Hydroxyl no. | 10–15 |
| Iodine no. | 12 max. |
| Moisture | 0.2% max. |
| Saponification no. | 1.0 max. |
| Specific gravity | 0.840 to 0.860 at 25° C. |
| Viscosity | 20–30 cps. at 25° C. |
| Volatile matter | No distillable matter at 5 mm. up to 150° C. | and when present is usually in a concentration of 5 to 30% (w/w).

A multi-sterol extract containing pure lanolin sterols and higher alcohols in their free forms only is sold under the trademark Amerchol ® CAB by Amerchol, supra. Amerchol ® CAB has the following properties as described in the Amerchol Laboratory Handbook for Cosmetics and Pharmaceuticals supplied by Amerchol in 1977.

| | |
| --- | --- |
| Appearance | pale cream, soft solid |
| Odor | faint, characteristic sterol |
| Water soluble acids and alkalies (USP XVI, p. 805) | neutral to litmus |
| Acid no. | 1.0 max. |
| Ash | 0.2% max. |
| Melting range (USP XVI Class II substances) | 40 to 46° C. |
| Moisture | 0.2% max. |
| Saponification no. | 1.0 max. |
| Volatile matter | no distillable matter at 5 mm. up to 150° C. |

A multi-sterol absorption base containing cholesterol esters as well as free sterols is sold under the trademark Amerchol ® H-9 by Amerchol, supra. Amerchol ® H-9 has the following properties as described in the Amerchol Laboratory Handbook for Cosmetics and Pharmaceuticals supplied by Amerchol in 1977:

| | |
| --- | --- |
| Appearance | pale yellow, soft solid |
| Odor | slight characteristic sterol |
| Water soluble acids and alkalies (USP XVI, p. 805) | neutral to litmus |
| Acid no. | 1.0 max. |
| Ash | 0.2% max. |
| Melting range (USP XVI, Class II substances) | 55–62° C. |
| Moisture | 0.2% max. |
| Saponification no. | 15–27 | and when present is usually in a concentration of 5 to 20%.

A hypoallergenic liquid fraction of acetylated lanolin alcohols which reduces the "greasiness" of normally oily or greasy anhydrous formulations such as ointments is sold under the trademark Acetulan ® by Amerchol, supra. Acetulan ® has the following properties as described in the Amerchol Laboratory Handbook for Cosmetics and Pharmaceuticals supplied by Amerchol in 1977:

| Appearance | pale yellow, thin oily liquid |
| --- | --- |
| Odor | practically odorless |
| Water soluble acids and alkalies (USP XVI, p. 805) | neutral to litmus |
| Acid no. | 1.0 max. |
| Ash | 0.2% max. |
| Hydroxyl no. | 8.0 max. |
| Iodine no. | 8–12 |
| Moisture | 0.2% max. |
| Saponification no. | 180–200 |
| Specific gravity | 0.850–0.880 at 25° C. |
| Viscosity | 10 cps. approx., at 25° C. | and when present is usually in a concentration of 5 to 10% (w/w).

An ethylene oxide ether of a select fraction of lanolin alcohols and sterols is sold under the trademark Solulan ® 5 by Amerchol, supra. The nonionic surface active lanolin derivative is compatible with nonionic systems and is a versatile formulating material for anhydrous pharmaceuticals. Solulan ® 5 has the following properties as described in the Amerchol Laboratory Handbook for Cosmetics and Pharmaceuticals supplied by Amerchol in 1977.

| Appearance | yellow semisolid |
| --- | --- |
| Odor | practically odorless |
| pH of 10% aqueous solution | 4.5–7 |
| Acid value | 3 max. |
| Ash | 0.3% max. |
| Hydroxyl value | 120–135 |
| Iodine value | 20–30 |
| Moisture | 1.5% max. |
| Saponification value | 10 max. |
| Interfacial tension (1% in 70 vis. mineral oil/water at 38° C.) | 1.6 dynes/cm. | and when present is usually in a concentration of 5 to 10% (w/w).

A liquid acetylated ethoxylated ester-ether lanolin derivative is sold under the trademark Solulan ® 97 by Amerchol, supra. It is completely acylated by reacting hydrophilic polyoxyethylene chains with lipophilic groups of lanolin origin. It is useful in topical pharmaceuticals and has the following properties as described in the Amerchol Laboratory Handbook for Cosmetics and Pharmaceuticals supplied by Amerchol in 1977.

| Appearance | light amber viscous liquid |
| --- | --- |
| Odor | faint-pleasant |
| pH of 10% aq. soln. | 4.5–7.0 |
| Acid no. | 3.0 max. |
| Hydroxyl no. | 10 max. |
| Saponification no. | 110–130 |
| Specific gravity | 1.040–1.060 at 25° C. | and when present is usually in a concentration of 5 to 10%.

The ointment formulations of the present invention are made by methods well known to those skilled in the art. More particularly, the polyoxypropylene 15 stearyl ether is heated to about 50°–70°. The anti-inflammatory steroid is added to the warmed polyoxypropylene 15 stearyl ether with stirring. The stirring is continued until the anti-inflammatory steroid is dissolved. The pharmaceutically acceptable carriers are mixed together and heated to approximately the same temperature (60°–70°) as the steroid mixture. The warmed mixture of pharmaceutically acceptable carriers is then added to the warmed steroid mixture with continuous stirring and/or agitation. The stirring is continued while the mixture is cooled to 40°.

Non-aqueous solutions utilize pharmaceutically acceptable non-aqueous liquid carriers. Pharmaceutically acceptable non-aqueous liquid carriers include, for example, mineral oil and light mineral oil. The solutions of the present invention are formulated by methods well known to those skilled in the art. The anti-inflammatory steroid is dissolved in the polyoxypropylene 15 stearyl ether with or without heat. Heating to 60°–70° is preferable as the solution process proceeds much more rapidly. The steroid solution is then diluted with a pharmaceutically acceptable liquid carrier and packaged in an appropriate container.

When any of the pharmaceutical carriers of present invention exist in U.S.P. or N.F. grade, the U.S.P. or N.F. grade may or may not be used. For example, non-U.S.P. white petrolatum is acceptable even though there is a U.S.P. grade of white petrolatum.

The pharmaceutical compositions of the present invention may be more fully understood from the following examples which are illustrative of the compositions of the present invention but are not to be construed as limiting.

EXAMPLE 1

Ointment without multi-sterol extract

| Ingredient | % |
| --- | --- |
| Anti-inflammatory steroid | 0.005–0.1 |
| Polyoxypropylene 15 stearyl ether | 1–40 |
| Glyceryl monostearate, self-emulsifying | 1–25 |
| White petrolatum | 35–98 |

Heat the polyoxypropylene 15 stearyl ether to 60°–70°, add the anti-inflammatory steroid with stirring until dissolved. The remaining ingredients are mixed, heated to 60°–70° and are added to the steroid solution. The mixture is stirred while cooling to 40°.

The ointment is packaged in appropriate containers.

EXAMPLE 2

Ointment with multi-sterol extract

| Ingredient | % |
| --- | --- |
| Anti-inflammatory steroid | 0.005–0.01 |
| Polyoxypropylene 15 stearyl ether | 1–40 |
| Multi-sterol extract | 5–40 |
| Cetyl palmitate | 5–20 |
| White Petrolatum | 35–89 |

Heat the polyoxypropylene 15 stearyl ether to 60°–70°. Add the anti-inflammatory steroid with stirring until dissolved. The remaining ingredients are mixed, heated to 60°-70° and are added to the steroid solution. The mixture is stirred while cooling to 40°.

The ointment is packaged in appropriate containers.

EXAMPLE 3

| Diflorasone Diacetate 0.05% ointment | |
|---|---|
| Ingredient | % |
| Diflorasone diacetate | 0.05 |
| Polyoxypropylene 15 stearyl ether[1] | 15.00 |
| Stearic acid U.S.P. | 15.00 |
| Multi-sterol extract | 10.00 |
| White petrolatum U.S.P. | 59.95 |

[1] Arlamol® E

Heat the polyoxypropylene 15 stearyl ether to 60°-70°. Add diflorasone diacetate with stirring until dissolved. The stearic acid, multi-sterol extract and white petrolatum are mixed, heated to 60°-70° and are added to the steroid solution. The mixture is stirred and/or agitated while cooled to 40°.

The ointment is packaged in appropriate containers.

EXAMPLE 4

| Betamethasone Valerate 0.05% ointment | |
|---|---|
| Ingredient | % |
| Betamethasone valerate | 0.05 |
| Polyoxypropylene 15 stearyl ether | 20.00 |
| Glyceryl monostearate, self-emulsifying | 15.00 |
| White petrolatum | 64.95 |

Following the general procedure of Example 1 the above ingredients are compounded into an ointment.

EXAMPLE 5

| Fluocinonide 0.01% ointment | |
|---|---|
| Ingredients | % |
| Fluocinonide | 0.01 |
| Polyoxypropylene 15 stearyl ether | 20.00 |
| Stearyl alcohol | 7.50 |
| Cetyl alcohol | 7.50 |
| White petrolatum | 64.99 |

Following the general procedure of Example 1 the above ingredients are compounded into an ointment.

EXAMPLE 6

| Fluocinolone Acetonide 0.05% ointment | |
|---|---|
| Ingredients | % |
| Fluocinolone acetonide | 0.05 |
| Polyoxypropylene 15 stearyl ether[1] | 30.00 |
| Glyceryl monostearate, self-emulsifying | 15.00 |
| White petrolatum | 54.95 |

[1] Arlamol® E

Following the general procedure of Example 1 the above ingredients are compounded into an ointment.

EXAMPLE 7

| Clobetasol propionate 0.025% ointment | |
|---|---|
| Ingredients | % |
| Clobetasol propionate | 0.025 |
| Polyoxypropylene 15 stearyl ether | 15.00 |
| Multi-sterol extract[1] | 25.00 |
| Stearic acid | 15.00 |
| White petrolatum | 44.975 |

[1] Amerchol® CAB

Following the general procedure of Example 2 the above ingredients are compounded into an ointment.

EXAMPLE 8

| Diflorasone diacetate 0.05% solution | |
|---|---|
| Ingredients | % |
| Diflorasone diacetate | 0.05 |
| Polyoxypropylene 15 stearyl ether | 44.00 |
| Light mineral oil N.F. viscosity 85 | 55.95 |

The diflorasone diacetate is dissolved in the polyoxypropylene 15 stearyl ether, while heating at 60°-70°, with stirring. The light mineral oil is added and the mixture stirred until uniform.

The solution is packaged in an appropriate container.

EXAMPLE 9

| Betamethasone Valerate 0.05% solution | |
|---|---|
| Ingredients | % |
| Betamethasone valerate | 0.05 |
| Polyoxypropylene 15 stearyl ether | 27.50 |
| Light mineral oil N.F. viscosity 85 | 72.45 |

Following the general procedure of Example 8 the above ingredients are compounded into a solution.

EXAMPLE 10

| Fluocinonide 0.05% solution | |
|---|---|
| Ingredients | % |
| Fluocinonide | 0.05 |
| Polyoxypropylene 15 stearyl ether | 88.95 |
| Light mineral oil N.F. viscosity 85 | 11.00 |

Following the general procedure of Example 8 the above ingredients are compounded into a solution.

I claim:

1. A pharmaceutical composition in ointment form for topical application which comprises an anti-inflammatory effective amount of an anti-inflammatory steroid selected from the group consisting of diflorasone diacetate, betamethasone valerate fluocinonide, clobetasol propionate, methylprednisolone acetate, fluorometholone, fluocinolone acetonide, hydrocortisone acetate, fludrocortisone, flumethasone and triamcinolone acetonide and 1 thru 40% of polyoxypropylene 15 stearyl ether.

2. A pharmaceutical composition according to claim 1 where the polyoxypropylene 15 stearyl ether is present in 15 thru 40%.

3. A pharmaceutical composition according to claim 2 where the anti-inflammatory steroid is diflorasone diacetate.

4. A pharmaceutical composition according to claim 3 where the anti-inflammatory effective amount of diflorasone diacetate is 0.01–0.1%.

5. A pharmaceutical composition according to claim 2 where the anti-inflammatory steroid is betamethasone valerate.

6. A pharmaceutical composition according to claim 2 where the anti-inflammatory steroid is fluocinonide.

7. A pharmaceutical composition according to claim 2 where the anti-inflammatory steroid is fluocinolone acetonide.

8. A pharmaceutical composition according to claim 2 where the anti-inflammatory steroid is clobetasol propionate.

9. A pharmaceutical composition in nonaqueous solution form for topical application which comprises an anti-inflammatory effective amount of an anti-inflammatory steroid selected from the group consisting of diflorasone diacetate, betamethasone valerate, fluocinonide, clobetasol propionate, methylprednisolone acetate, fluorometholone, fluocinolone acetonide, hydrocortisone acetate, fludrocortisone, flumethasone and triamcinolone acetonide and a solubilizing effective amount of polyoxypropylene 15 stearyl ether.

10. A pharmaceutical composition according to claim 9 where the anti-inflammatory steroid is diflorasone diacetate.

11. A pharmaceutical composition in ointment form comprising 0.01–0.1% of diflorasone diacetate, 1–40% of polyoxypropylene 15 stearyl ether and pharmaceutically acceptable carriers.

12. A pharmaceutical composition in ointment form comprising

| Ingredient | % |
|---|---|
| Diflorasone diacetate | 0.01–0.10 |
| Polyoxypropylene 15 stearyl ether | 5–30 |
| Stearic acid | 5–20 |
| Multi-sterol extract | 5–30 |
| White petrolatum | 20–85 |

13. A pharmaceutical composition in ointment form comprising

| Ingredient | % |
|---|---|
| Diflorasone diacetate | 0.05 |
| Polyoxypropylene 15 stearyl ether | 15.00 |
| Stearic acid U.S.P. | 15.00 |
| Multi-sterol extract | 10.00 |
| White petrolatum U.S.P. | 59.95 |

* * * * *